US 7,946,152 B2

(12) United States Patent
Saito et al.

(10) Patent No.: US 7,946,152 B2
(45) Date of Patent: May 24, 2011

(54) APPARATUS AND METHOD FOR MEASURING THE CONCENTRATION OF ORGANIC GAS

(75) Inventors: Misako Saito, Nirasaki (JP); Teruyuki Hayashi, Nirasaki (JP)

(73) Assignee: Tokyo Electron Limited, Tokyo (JP)

(*) Notice: Subject to any disclaimer, the term of this patent is extended or adjusted under 35 U.S.C. 154(b) by 674 days.

(21) Appl. No.: 11/916,842

(22) PCT Filed: Jun. 2, 2006

(86) PCT No.: PCT/JP2006/311114
§ 371 (c)(1),
(2), (4) Date: Dec. 7, 2007

(87) PCT Pub. No.: WO2006/132156
PCT Pub. Date: Dec. 14, 2006

(65) Prior Publication Data
US 2009/0113991 A1    May 7, 2009

(30) Foreign Application Priority Data
Jun. 7, 2005    (JP) .................. 2005-167545

(51) Int. Cl.
*G01N 33/00* (2006.01)
*G01N 7/00* (2006.01)
(52) U.S. Cl. ..................... 73/31.02; 73/31.07

(58) Field of Classification Search ............. 73/31.01, 73/31.02, 31.03, 31.07
See application file for complete search history.

(56) References Cited

FOREIGN PATENT DOCUMENTS

| JP | 10 111224 | 4/1998 |
|---|---|---|
| JP | 11 64316 | 3/1999 |
| JP | 2003 14713 | 1/2003 |
| JP | 2003 307511 | 10/2003 |
| JP | 2003 315221 | 11/2003 |
| JP | 3494945 | 11/2003 |
| JP | 3641592 | 1/2005 |
| WO | 2004 077015 | 9/2004 |

*Primary Examiner* — Daniel S Larkin
(74) *Attorney, Agent, or Firm* — Oblon, Spivak, McClelland, Maier & Neustadt, L.L.P.

(57) ABSTRACT

In a measuring apparatus, an atmosphere to be inspected taken out from a space to be inspected in a processing system is analyzed for organic gas concentration. The apparatus is provided with a collector having an approach connected to the space to be inspected. The collector is connected to a gas exhaust system and an adsorption material for preparing a captured organic gas is held in the collector. A temperature control mechanism including a heater controls the adsorption/desorption of organic gas through temperature control of the adsorption material. A carrier gas is supplied from a carrier gas supplying system in order to transfer the desorbed gas taken from the captured organic gas and the concentration of organic gas in the carrier gas transferring the desorbed gas is determined in a concentration measuring unit.

8 Claims, 10 Drawing Sheets

APPARATUS AND METHOD FOR MEASURING THE CONCENTRATION OF ORGANIC GAS

FIELD OF THE INVENTION

The present invention relates to an apparatus and method for measuring the concentration of organic gas included in an atmosphere to be inspected that has been taken out from a space to be inspected in a processing system such as a semiconductor processing system. The term "semiconductor processing" used herein implies various processes to manufacture semiconductor devices or structures including wiring, electrodes and the like connected thereto on a target object e.g., a semiconductor wafer or a glass substrate for an LCD (Liquid Crystal Display) or an FPD (Flat Panel Display), by forming a semiconductor layer, an insulating layer, a conduction layer and the like in specified patterns on the target object.

BACKGROUND OF THE INVENTION

In general, to manufacture a semiconductor integrated circuit, various processes such as film forming, etching, oxidation and diffusion are performed on a target object such as a semiconductor wafer in a semiconductor processing system. In this case, the production yield of a wafer where microprocessing is performed at a submicron level needs to be improved. For this, an atmosphere in a wafer transfer area of a processing apparatus, as well as in a clean room in which the processing apparatus (semiconductor manufacturing apparatus) is installed, is strictly managed. Therefore, fine particles or an organic gas in the atmosphere that may cause defects in products are removed (see, for example, Japanese Patent Application Publication Nos. 2002-75844 and 2002-151372).

To be specific, fine particles are usually removed by an ULPA (ultra low penetration air) filter. The organic gas is removed by an organic gas removal filter formed of a chemical filter such as activated carbon. For example, chemical filters or ULPA filters are disposed at a ceiling portion of the clean room that accommodates the processing apparatus, forming a downstream current of clean air. Further, the processing apparatus has a handling space for handling the wafer or a stocking space for storing the wafer at its front end portion to transport the wafer to a processing chamber. Chemical filters or ULPA filters are usually installed at a ceiling portion or a lateral side portion of the handling space or a stocking space to form a laminar flow of clean gas (e.g., air or $N_2$ gas).

However, once reaching a specific adsorption amount of the ULPA filter or the organic gas removal filter, the collecting ability thereof decreases rapidly. Therefore, in order to keep the production yield high, it is necessary to find out the lifetime of the filter accurately.

Hereinafter, how to manage the lifetime of the organic gas removal filter, for example, will be described. First, the atmosphere that has passed through the organic gas removal filter in the clean room or the processing apparatus is made to go through an adsorptive material for organic gas for a specified amount of time or at a specified flow rate. Thus, organic gas having remained in the atmosphere are completely adsorbed and collected by the adsorptive material. The adsorptive material that has adsorbed the organic gas is then transferred to a measurement specialist. Then, the measuring specialist heats the adsorptive material to completely desorb the organic gas having been adsorbed thereto, and measures the concentration of the desorbed organic gas.

Thereafter, based on the measurement result obtained by the measuring specialist, it is determined whether the lifetime of the organic gas removal filter comes to an end. For example, if the organic gas concentration at the measuring point of time was higher than a reference value, it means that the organic gas is not sufficiently removed by the filter. That is, the lifetime of the filter is deemed to have expired. This also applies to a filter for removing an amine gas, which is a kind of organic gas.

SUMMARY OF THE INVENTION

It is an object of the present invention to provide an apparatus and method for measuring the concentration of organic gas in an atmosphere to be inspected in real time.

It is another object of the present invention to provide an apparatus and method for selectively measuring the concentration of organic gas which tend to be easily adsorbed on a target object.

In accordance with an embodiment of the present invention, there is provided a concentration measuring apparatus for measuring a concentration of organic gas contained in an atmosphere to be inspected taken out from a space to be inspected in a processing system, the apparatus including a collector having an inlet port connected to the space to be inspected for introducing thereto the atmosphere to be inspected; a gas exhaust system, connected to the collector, for introducing the atmosphere to be inspected into the collector by exhausting an inside of the collector; an adsorption member, accommodated in the collector, for adsorbing organic gas included in the atmosphere to be inspected to obtain a collected gas; a temperature control unit having a heater for controlling an adsorption and a desorption of organic gas by adjusting the temperature of the adsorption member; a carrier gas supplying unit for supplying the collector with a carrier gas for conveying a desorbed gas desorbed from the collected gas by heating the adsorption member; a concentration measuring unit, connected to the collector, for measuring the concentration of organic gas in the carrier gas that is carrying the desorbed gas; and a control unit for controlling the concentration measuring apparatus.

In accordance with another embodiment of the present invention, there is provided a concentration measuring method for measuring a concentration of organic gas contained in an atmosphere to be inspected taken out from a space to be inspected in a processing system, the method including introducing the atmosphere to be inspected into a collector having an inlet port connected to the space to be inspected by exhausting the collector; obtaining a collected gas by adsorbing organic gas contained in the atmosphere by an adsorbing member accommodated in the collector;

taking out a desorbed gas from the collected gas by heating the adsorption member; transferring the desorbed gas by supplying carrier gas into the collector; and measuring the concentration of organic gas in the carrier gas that is carrying the desorbed gas.

DETAILED DESCRIPTION OF THE EMBODIMENTS

Figure 1:
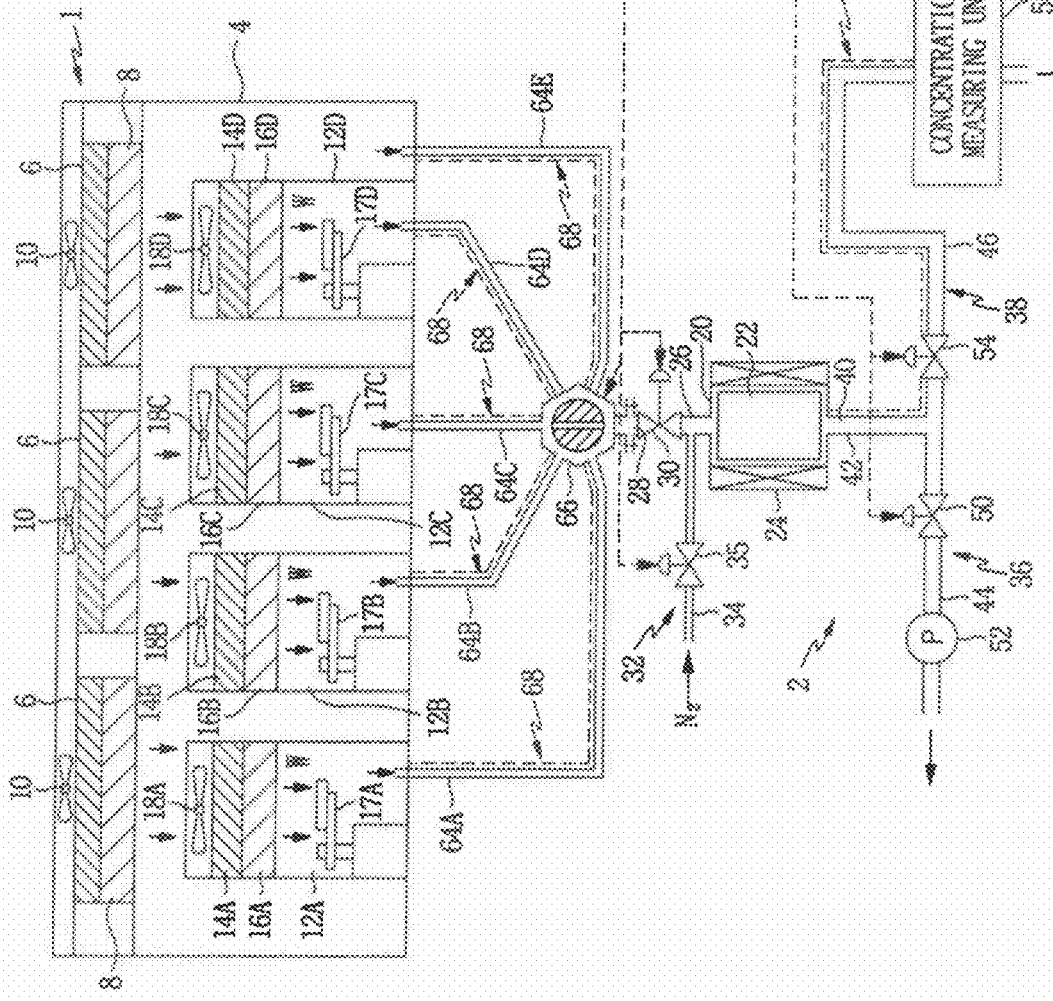
FIG. 1 is a configuration view showing the relationship among an organic gas concentration measuring apparatus, a processing apparatus and a clean room in a processing system in accordance with an embodiment of the present invention.

While developing the present invention, the inventors researched the problems in the conventional methods for measuring the organic gas concentration or determining the lifetime of filters and solutions thereto. As a result, the inventors have acquired knowledge to be described below.

According to the conventional methods as above, the operation of adsorbing and collecting an organic gas by the adsorptive material and the operation of inspecting the organic gas desorbed by heating are performed in different places. Therefore, the atmosphere filtered by the organic gas removal filter has to be regularly monitored. That is, it is difficult to determine in real time whether the organic gas removal filter has reached its lifetime, i.e., whether it entered the breakthrough state.

In this case, the organic gas removal filter has to be replaced earlier than the end of its lifetime, which causes an increase in the running cost. Further, since the operation of adsorbing and collecting the organic gas and the operation of inspecting them are performed in different places, the entire operations become complicated, and the measurement cost increases significantly.

Further, according to the conventional methods, all gas materials contained in the organic gas are subject to the concentration measurement, regardless of whether each of the gas materials is easily adsorbed onto the semiconductor wafer. Therefore, there is a tendency that the lifetime of the filter is regarded to be shorter than its actual lifetime, thereby causing an increase in the running cost.

Further, since amine includes many kinds of compounds, the lifetime of its filter cannot be calculated exactly, thus making it difficult to determine the lifetime thereof. In addition, amine is liable to be decomposed, so it is difficult to measure the concentration thereof existing in an atmosphere.

Hereinafter, the embodiments of the present invention conceived from the above knowledge will be described with reference to the accompanying drawings. Further, in the description below, same reference numerals are used to designate elements substantially same in function and configuration, and an explanation will be not repeated unless necessary.

(Concentration Measurement for Organic Gas)

Figure 2:
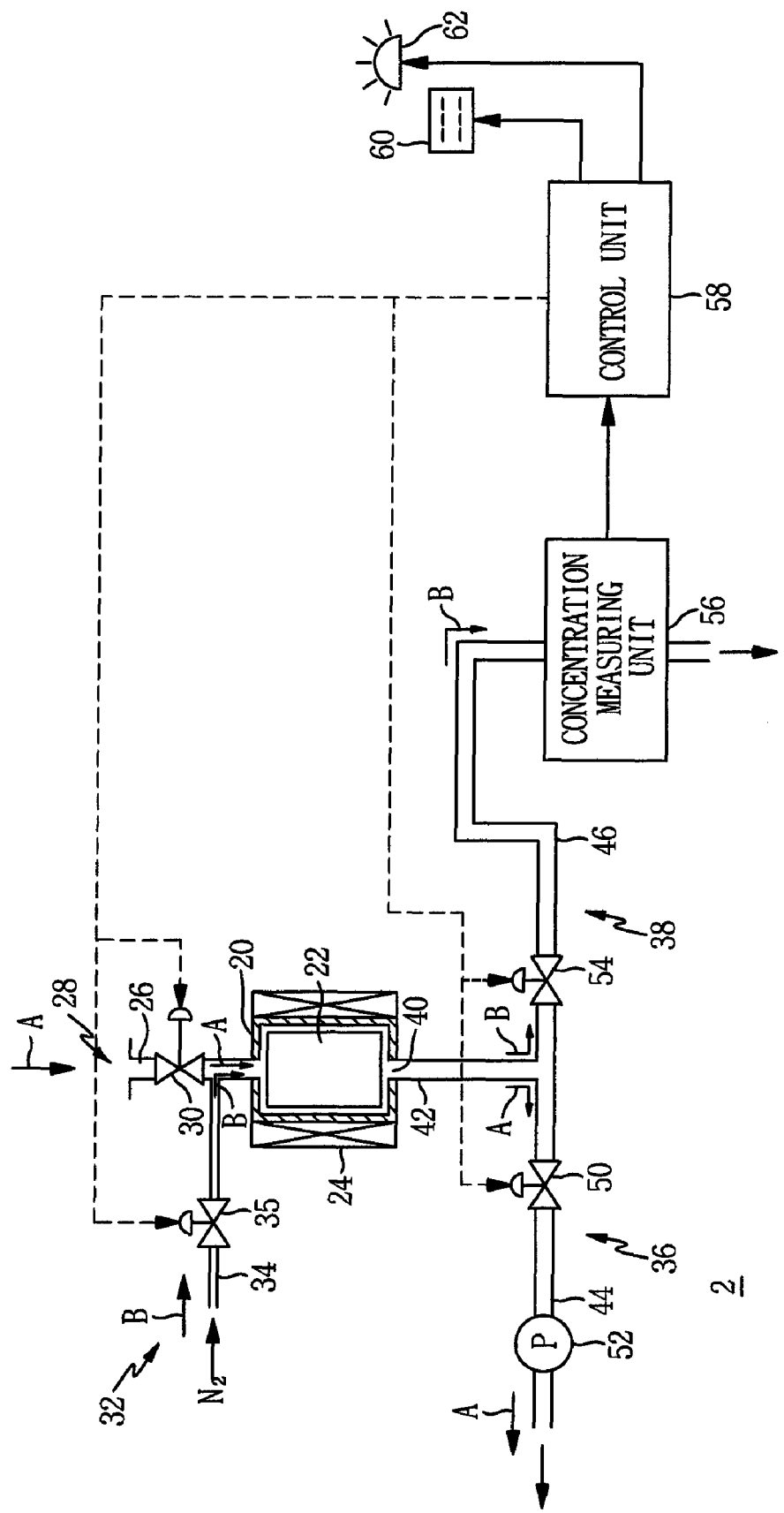
FIG. 2 is a configuration view illustrating the organic gas concentration measuring apparatus shown in FIG. 1.

FIG. 1 is a configuration view showing the relationship among an organic gas concentration measuring apparatus, a processing apparatus and a clean room in a processing system in accordance with an embodiment of the present invention. FIG. 2 is a configuration view illustrating the organic gas concentration measuring apparatus shown in FIG. 1. As shown in FIG. 1, an organic gas concentration measuring apparatus 2 is disposed in a processing system 1 to detect the concentration of organic gas in an atmosphere of the processing apparatus or a clean room 4 where the processing apparatus is installed.

Organic gas removal filters 6, which are chemical filters made of activated carbon, are disposed at a partial or entire ceiling portion of the clean room 4. ULPA filters 8 for removing particles are respectively disposed below the filters 6. A blower 10 is arranged above each of the organic gas removal filters 6. In this manner, a downstream current of clean air with a high degree of cleanliness, from which particles and organic gas have been removed, is formed in the clean room 4. The clean air is exhausted via a plurality of gas exhaust ports (not shown) formed at a bottom surface.

One or more processing apparatuses are installed inside of the clean room 4. In the drawing, there are four processing apparatuses 12A to 12D installed. A processing chamber (not shown) is disposed in each of the processing apparatuses, where specified processes are performed on a semiconductor wafer. However, the number of the processing apparatuses is not limited thereto. Further, each of the processing apparatuses 12A to 12D has a transfer area under an atmospheric pressure, at which the wafer is transferred, such as a handling space for handling the wafer or a stocking space for storing the wafer. Transfer arms 17A to 17D for transferring the wafer W are disposed in the transfer areas, respectively.

In the same manner as the clean room 4, organic gas removal filters 14A to 14D, which are chemical filters made of activated carbon, and ULPA filters 16A to 16D are respectively disposed at ceiling portions of the transfer areas in a manner that the organic gas removal filters 14A to 14D and the ULPA filters 16A to 16D are stacked with each other. Blowers 18A to 18D are arranged above the organic gas removal filters 14A to 14D, respectively. Thus, a downstream current of clean air with a high degree of cleanliness, from which particles and organic gas have been removed, or a downstream current of clean gas such as nitrogen is formed in each of the transfer areas. By specifying the atmosphere of the transfer area in each of the processing apparatus 12A to 12D or the atmosphere of the clean room 4 as an atmosphere to be inspected, organic gas contained therein is inspected as described later.

Next, the organic gas concentration measuring apparatus 2 will be explained. The organic gas concentration measuring apparatus 2 includes, for example, a cylindrical collector 20 made of, e.g., glass. The collector 20 accommodates therein or is filled up with an adsorptive material 22 that serves as an adsorption member for adsorbing the organic gas. For example, TENAX-TA (product name) may be used as the adsorptive material 22. Installed at a sidewall of the collector 20 is a heater 24 formed of a resistance heater or the like. A temperature control unit including the heater 24 controls the adsorption and desorption of the organic gas by adjusting the temperature of the adsorptive material 22. For example, by heating the adsorptive material 22 in the collector 20, the temperature control unit allows the adsorbed gas to be desorbed, or prevents the adsorption of a specific kind of organic gas that has given properties. Further, the adsorption member for adsorbing the organic gas is not limited to the adsorptive material 22, and may be configured by various types of material with a chemical and/or physical adsorption function.

A gas inlet line 26 is coupled to a ceiling portion of the collector 20, and an upper portion of the gas inlet line 26 is connected to a gas inlet port 28 for introducing the atmosphere to be inspected. The gas inlet line 26 in a vicinity of the gas inlet port 28 is provided with a switching valve 30 for opening and closing the gas inlet line 26 when necessary. Installed at the gas inlet line 26 is a carrier gas supplying unit 32 that supplies a carrier gas for conveying the organic gas desorbed from the adsorptive material 22 (i.e., desorbed gases). The carrier gas supplying unit 32 includes a gas line 34 connected to the gas inlet line 26 at a location between the switching valve 30 and the collector 20. A switching valve 35 is installed in the gas line 34 to supply the collector 20 with carrier gases maintained at a specific pressure if necessary. For example, an $N_2$ gas, an inert gas such as He or Ar, or air with a high degree of cleanliness may be used as the carrier gas.

A gas exhaust system 36, which functions to discharge the atmosphere in the collector 20 when the atmosphere to be inspected is introduced thereto, is coupled to a bottom portion of the collector 20. Further, a gas mixing system 38, which transports the carrier gases together with the organic gas desorbed from the adsorptive material 22, is connected to the bottom portion of the collector 20. Specifically, an evacuation port 40, to which a discharge line 42 is connected, is formed at the bottom portion of the collector 20. A gas exhaust line 44 that forms a part of the gas exhaust system 36 and a gas line 46 that forms a part of the gas mixing system 38 are branched off from the discharge line 42. Alternatively, the gas exhaust line 44 and the gas line 46 may be directly connected to the bottom portion of the collector 20 without installing the discharge line 42 thereat.

A switching valve 50 and a gas exhaust pump 52 are arranged in the gas exhaust line 44 serially in the downstream order. The gas exhaust pump 52 discharges the atmosphere in the collector 20 when the atmosphere to be inspected is introduced thereto, i.e. when the organic gas is collected. Further, a switching valve 54 is installed in the gas line 46, and a concentration measuring unit 56 is disposed at an end of the gas line 46. The concentration measuring unit 56 measures the concentration of the desorbed organic gas in the carrier gases. Installed throughout the gas line 46 and the discharge line 42 is a heating unit 57, e.g., a tape heater for heating, to prevent the organic gas flowing in the lines 46 and 42 from being liquefied. The entire operations of the apparatus are controlled by a control unit 58 configured by, e.g., a microcomputer. The control unit 58 has a memory unit (not shown) for storing the measurement result of the concentration measuring unit 56 and a display unit 60 for displaying them. The display unit 60, for example, visually presents the measurement result to the operator.

The control unit 58 has a function of estimating the lifetime of the organic gas removal filter based on the measurement result of the concentration measuring unit 56. For this estimation, the control unit 58 may input and store therein a lifetime reference value of the organic gas removal filter. The control unit 58 further includes an alarm unit 62 for informing the operator that the lifetime of the organic gas removal filter has expired according to the measurement result. The alarm unit 62 informs the operator in a visual or auditory way or both, e.g., by voice or by lighting a lamp. Alternatively, the lifetime estimating function of the control unit 58 may be installed only if necessary. It is also possible that the operator detects the end of the lifetime of the organic gas removal filter by referring to the measurement result.

Further, atmosphere extraction lines 64A to 64E extends from the processing apparatuses 12A to 12D and the clean room 4, respectively. Four of the atmosphere extraction lines 64A to 64D extract the atmospheres from the transfer areas in the processing apparatuses 12A to 12D, respectively. The remaining one of the atmosphere extraction lines 64E extracts the atmosphere from the clean room 4. The atmosphere extraction lines 64A to 64E commonly communicate with the gas inlet port 28 in the gas inlet line 26.

A multi-way valve 66 formed of, e.g., a six-way valve in this example, serves as a selection valve, and is disposed at a part where the atmosphere extraction lines 64A to 64E join together. The gas inlet line 26 selectively communicates with one of the atmosphere extraction lines 64A to 64E by properly controlling the multi-way valve 66. Further, a heating unit 68 such as a tape heater for heating is disposed at the atmosphere extraction lines 64A to 64E with the six-way valve 66 and the gas inlet line 26, thereby preventing the liquefaction of the organic gas flowing therethrough.

Hereinafter, the operations of the organic gas concentration measuring apparatus as configured above will be described.

Schematically, in the case of adsorbing the organic gas in the atmosphere to be inspected, the gas exhaust pump 52 in the gas exhaust system 36 is operated as designated by an arrow A shown in FIG. 2. In this manner, the atmosphere to be inspected introduced from the gas inlet line 26 passes through the adsorptive material 22 in the collector 20, and is then discharged through the gas exhaust system 36. While the atmosphere to be inspected passes through the collector 20, the organic gas is adsorbed to be removed by the adsorptive material 22, whereby the collected organic gas is obtained.

The six-way valve 66, disposed at the part where the atmosphere extraction lines 64A to 64E join together, properly selects one of the atmosphere extraction lines 64A to 64E. Thus, an atmosphere to be measured is selected from the processing apparatuses 12A to 12D and the clean room 4. Further, at this point, the switching valve 35 in the carrier gas supplying unit 32 is closed to stop supplying the carrier gas. Furthermore, the switching valve 54 in the gas mixing system 38 is closed to prevent the atmosphere from flowing into the concentration measuring unit 56.

Thereafter, at the time of measuring the organic gas concentration, desorbed gases are obtained from the collected organic gas (the organic gas that has been adsorbed) by heating the adsorptive material 22 using the heater 24. Further, as indicated by an arrow B shown in FIG. 2, the carrier gas formed of $N_2$ gas is supplied from the carrier gas supplying unit 32, and then passes through the adsorptive material 22 in the collector 20. In this manner, the carrier gas is mixed with the desorbed gases, and then is discharged from the collector 20. The mixed gas is then transferred to the concentration measuring unit 56 via the gas mixing system 38. Then, the organic gas concentration is measured by the concentration measuring unit 56.

First Embodiment

Figure 3:
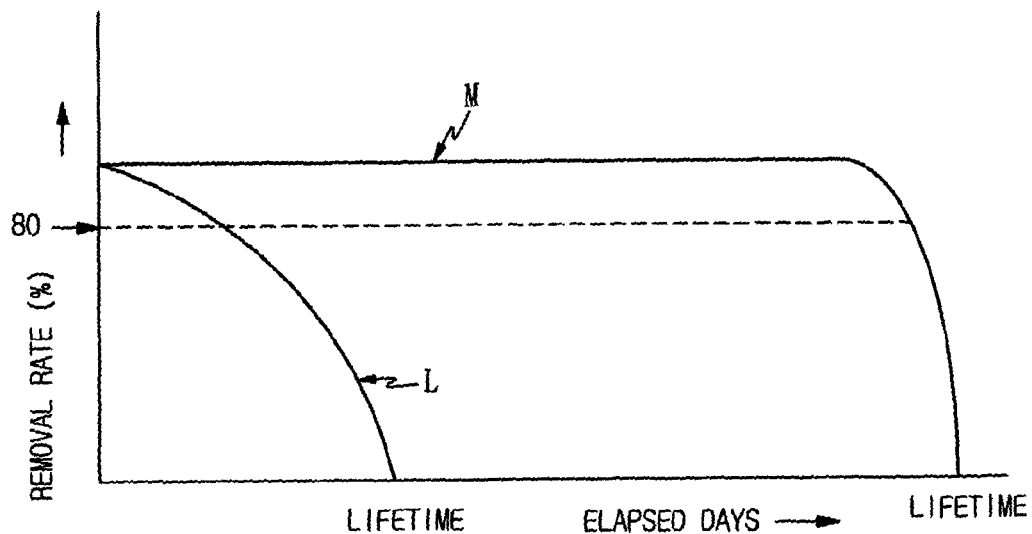
FIG. 3 is a graph showing the dependency of a removal rate of an organic gas removal filter on boiling points of organic materials.
Figure 4:
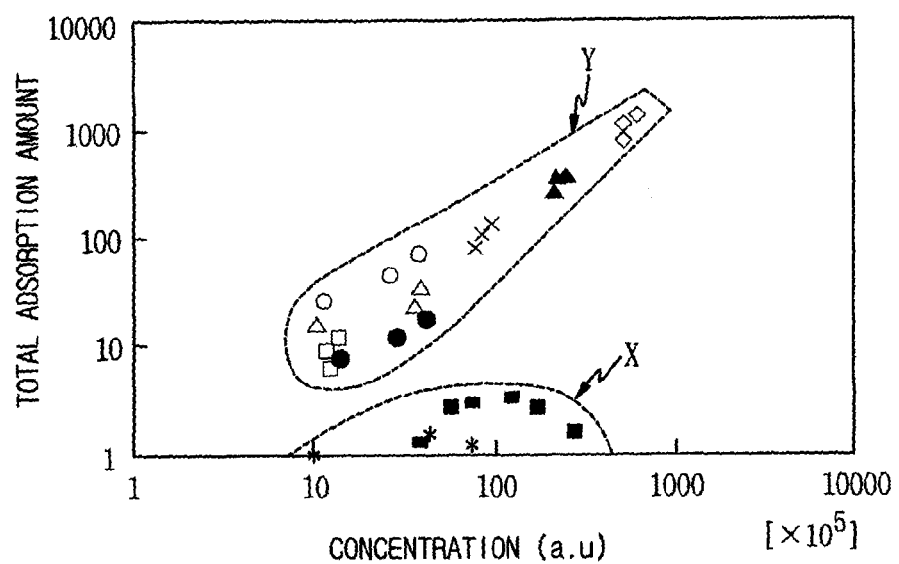
FIG. 4 is a graph representing the relationship between the organic gas concentration and the total adsorption amount of organic gas adsorbed onto a target silicon wafer.
Figure 5:
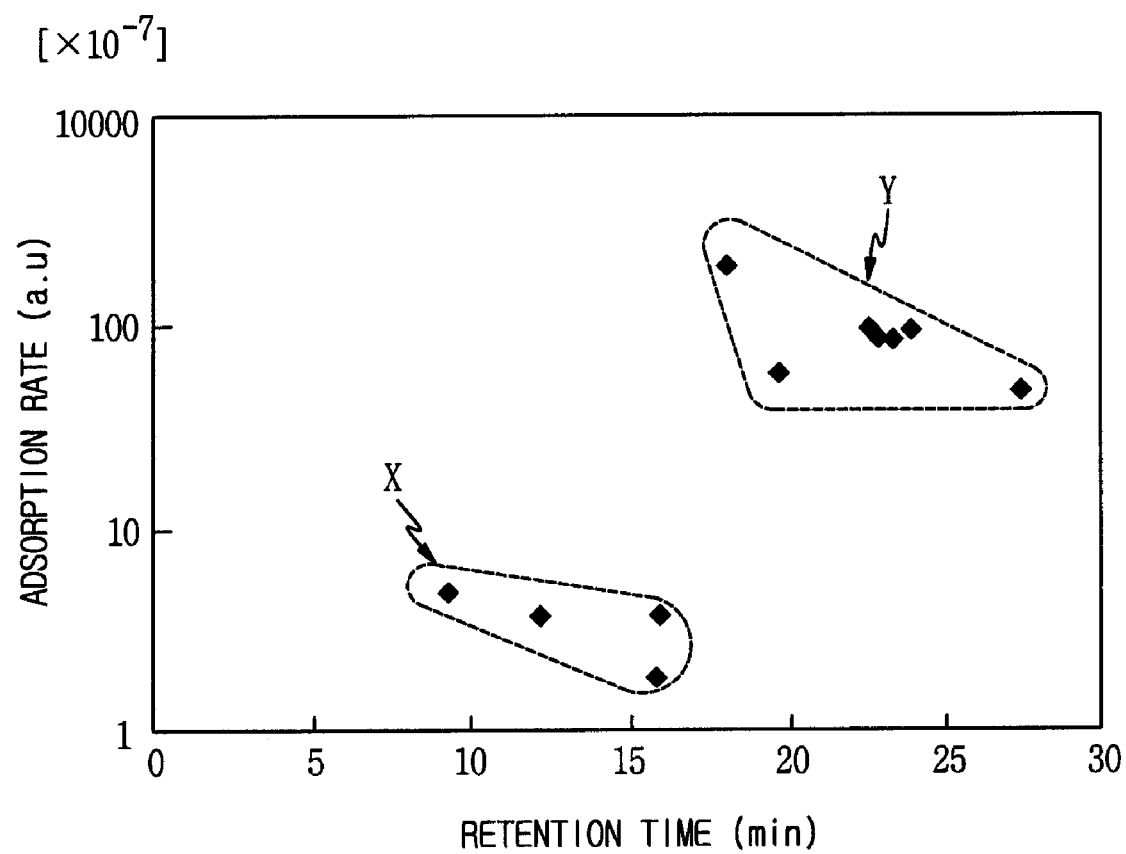
FIG. 5 is a graph describing the relationship between the retention time of the organic gas, which corresponds to the boiling point of organic materials thereof, and the adsorption rate of the organic gas onto the silicon wafer.
Figure 6:
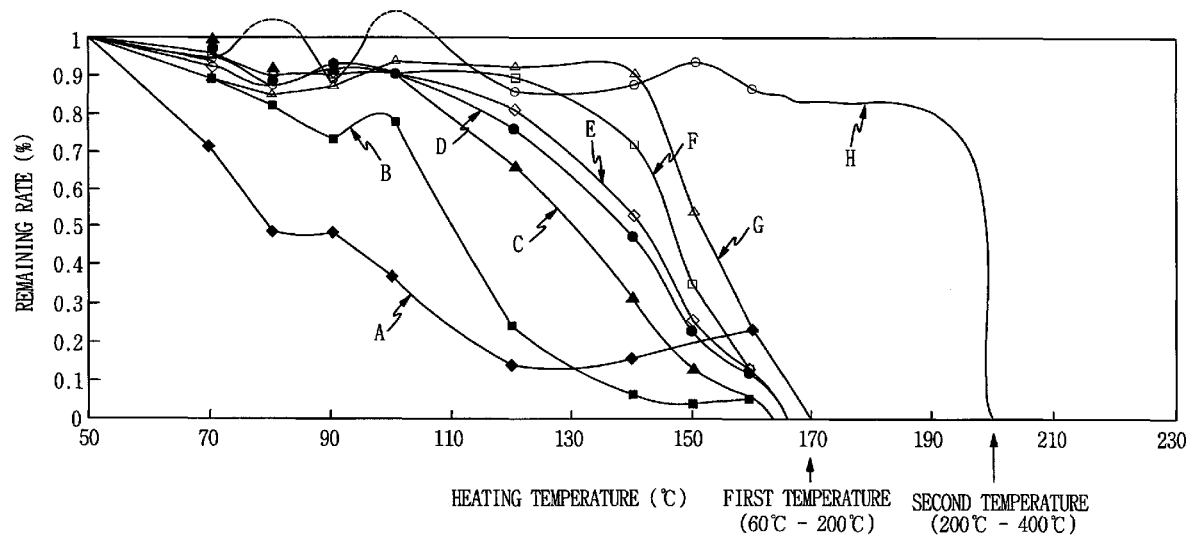
FIG. 6 is a graph illustrating the dependency of the relationship between the heating temperature of the adsorptive material and the remaining rate of the organic gas on the boiling point of organic materials.

FIG. 3 is a graph showing the dependency of a removal rate of an organic gas removal filter upon boiling points of organic materials. FIG. 4 is a graph representing the relationship between the organic gas concentration and the total adsorption amount of organic gas adsorbed on a target silicon wafer. FIG. 5 presents a graph describing the relationship between the retention time of organic gas, which corresponds to the boiling point of the organic material, and the adsorption rate of the organic gas onto the silicon wafer. FIG. 6 shows a graph illustrating the dependency of the relationship between the heating temperature of the adsorptive material and the remaining rate of organic gas upon the boiling point of organic materials.

In the method of the first embodiment, the organic gas concentration measuring apparatus 2 shown in FIGS. 1 and 2 is used. That is, the apparatus used for this method includes the collector 20 having the gas inlet port 28 for introducing thereto the atmosphere to be inspected. The collector 20 accommodates therein the adsorptive material 22 for collecting organic gas. Further, the heater 24 is installed for, if necessary, heating the adsorptive material 22 to desorb the organic gas collected by the adsorptive material 22.

Connected to the collector 20 is the gas exhaust system 36 for discharging the atmosphere in the collector 20 when the organic gas is adsorbed (i.e., the atmosphere to be inspected is introduced); the carrier gas supplying unit 32 for supplying a carrier gas to carry the desorbed organic gas; and the gas mixing system 38 for transporting the carrier gas together with the desorbed organic gas. The gas mixing system 38 includes the concentration measuring unit 56 for measuring the concentration of the desorbed organic gas in the carrier gas. The overall operations of the apparatus are controlled by the control unit 58.

In the present method, to desorb the organic gas from the adsorptive material 22, the adsorptive material 22 is heated in a two-step process involving a first temperature and a second temperature. The reason thereof is as follows.

In general, the organic gas removal filter adsorbs to trap the organic gas without depending on the boiling point of the organic material thereof. In other words, an organic gas material having a relatively low boiling point is adsorbed to be trapped as well as that having a relatively high boiling point. However, the lifetime of the organic gas removal filter varies greatly according to the boiling point of the organic material.

FIG. 3 is a graph showing the relationship between elapsed days and the organic gas removal rate of the organic gas removal filter. As indicated by a characteristic curve L, the removal rate of an organic gas material having a relatively low boiling point is so deteriorated to enter its breakthrough state in a relatively short time, which means that the lifetime thereof is short. However, as indicated by a characteristic curve M, the removal rate of an organic gas material having a relatively high boiling point remains high for a relatively long time, which means that the lifetime thereof until entering its breakthrough state is long.

Regarding the organic gas adsorbed onto a surface of the semiconductor wafer, an organic gas material having a relatively high boiling point is easily adsorbed onto the wafer surface provided that its concentration thereof is appropriate. On the other hand, an organic gas having a relatively low boiling point is hardly adsorbed onto the wafer surface irrespective of its concentration. In other words, by measuring the adsorption amount or concentration of the organic gas material having a relatively high boiling point, which is easily adsorbed onto the wafer surface, the lifetime of the organic gas removal filter can be estimated exactly. On the other hand, it would be preferable to exclude the organic gas material having a relatively low boiling point from the object of the measurement.

Verification experiments were performed as to the difficulty of adsorbing the organic gas onto the wafer surface depending on the boiling point. Hereinafter, the verification result will be described.

Herein, a target silicon wafer was arranged in the clean room atmosphere (wind speed of 0.3 m/sec) whose degree of cleanliness was class 10. Further, an organic gas adsorptive material (which is of the same kind as the adsorptive material 22 of the present embodiment) for collecting organic gas was disposed in the vicinity of the wafer to sample the organic gas in the air.

FIG. 4 represents the relationship between the organic gas concentration and the total amount of the organic gas adsorbed onto the target silicon wafer. In FIG. 4, a group X enclosed by a dotted line X represents a group of organic gas materials having relatively low boiling points, and a group Y enclosed by a dotted line Y represents a group of organic gas materials having relatively high boiling points. As is clear in the graph, the organic gas materials in the group X, which have relatively low boiling points, are hardly adsorbed onto the target silicon wafer regardless of the concentration of the organic gas in the atmosphere (i.e., do not cause a decrease in production yield). In contrast, in case of the organic gas materials in the group Y that have relatively high boiling points, the total amount of the organic gas adsorbed onto the target silicon wafer varies depending on the concentration of the organic gas in the atmosphere. Accordingly, the estimation of the lifetime of the organic gas removal filter should be verified by examining whether the filter can adsorb organic gas materials having relatively high boiling points in a sufficient amount.

FIG. 5 presents a graph describing the relationship between the retention time of the organic gas and the adsorption rate of the organic gas adsorbed onto the silicon wafer. Herein, the retention time is the elution time of a gas chromatography analysis device, and corresponds to the boiling point of the organic material. As is clear from the graph, the organic gas materials in the group X having relatively low boiling points are not easily adsorbed onto the target silicon wafer, and show extremely low adsorption rates. However, the organic gas materials in the group Y having relatively high boiling points are more easily adsorbed onto the target silicon wafer, and their adsorption rates are greater than those in the X group.

FIG. 6 shows a graph illustrating the relationship between the heating temperature of the adsorptive material having collected the organic gas and the remaining rate of the organic gas. This graph represents the amount of the organic gas that is not desorbed but remains in the adsorptive material while the organic gas is heated to be desorbed from the organic gas adsorptive material having collected the organic gas. The graph shows eight kinds of organic materials (i.e., gas A to gas H) with different boiling points. Gas A and gas B are organic gas materials with low boiling points; gas C to gas G are organic gas materials with relatively low boiling points; and gas H is an organic gas material with a relatively high boiling point.

The data shown in FIG. 6 has been obtained by the operations described below. First, each of the adsorptive materials was heated for ten minutes to each temperature plotted along the horizontal axis, thereby dispersing the organic gas desorbed at each temperature. Thereafter, the remaining organic gas was all dispersed by heating the adsorptive material to 280° C. At that time, the gas concentration was measured, and the remaining amount was acquired at each temperature.

As is clear from FIG. 6, there is a tendency that an organic material is desorbed at a lower temperature as it has a lower boiling point. The organic materials with low boiling points (gas A and gas B) are mostly desorbed at a heating temperature of 120° C. The organic materials with relatively low boiling points (gas C to gas G) are mostly desorbed at 170° C.

Further, the organic material with a relatively high boiling point (gas H) is rarely desorbed at a heating temperature of 170° C., and is mostly desorbed at 200° C. or higher. Therefore, it can be deduced that, when desorbing the organic gas from the adsorptive material, organic gas materials with relatively low boiling points and those with relatively high boiling points can be separated by changing the heating temperature of the adsorptive material in two steps as described above. In other words, the adsorptive material is first heated to a first temperature within a range from 60° C. to 200° C. for a given time, and then further heated to a second temperature of 200° C. or above. In this manner, the organic gas materials with relatively low boiling points can be separated from those with relatively high boiling points.

In accordance with the method of the first embodiment, by using the above characteristics, the concentration of only such organic materials having relatively high boiling points is measured. Then, the end of the lifetime of the organic gas removal filter is estimated on the basis of the measurement result.

Figure 7:
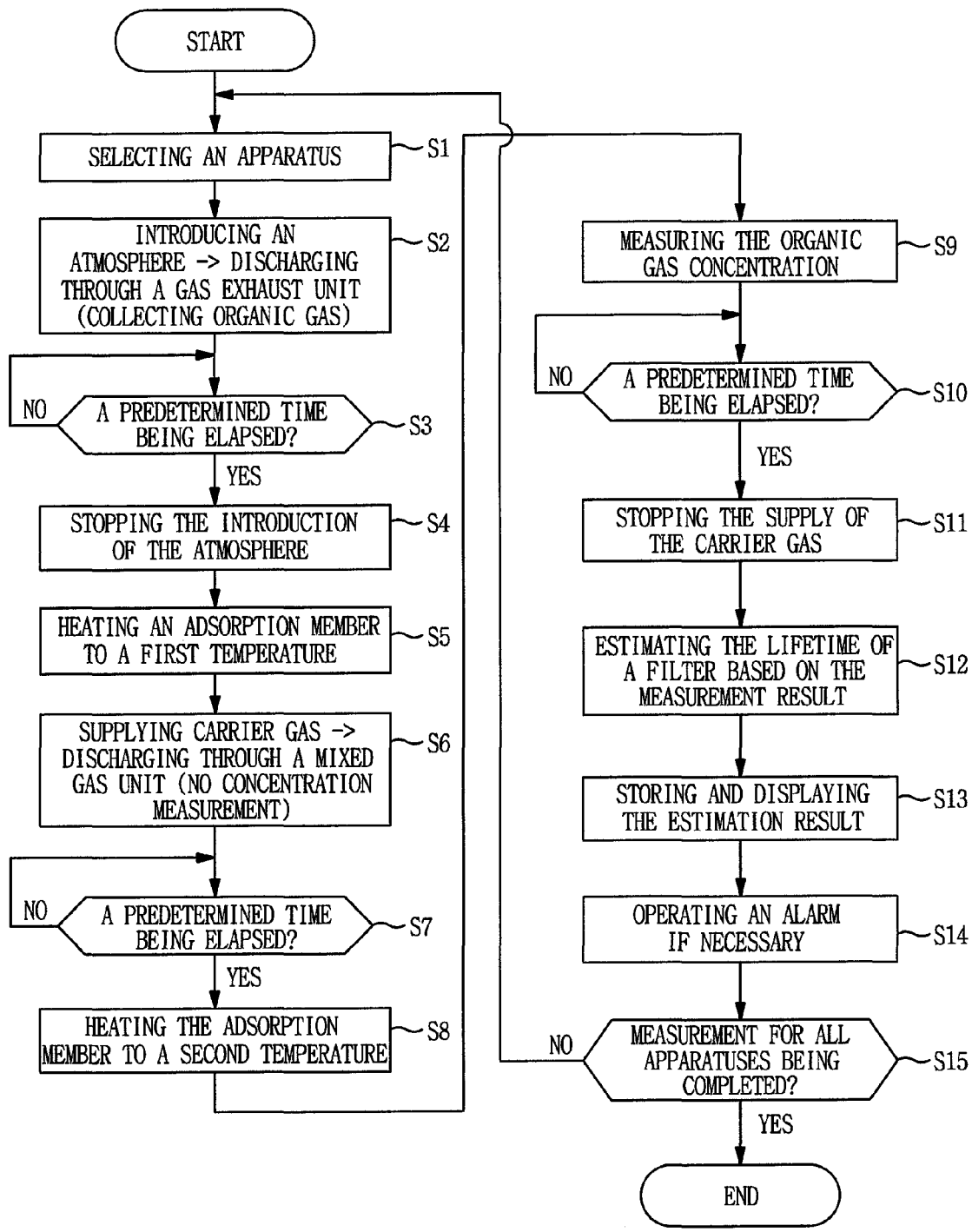
FIG. 7 is a flow chart for illustrating a sequence of the method in accordance with the first embodiment of the present invention.

FIG. 7 is a flow chart for illustrating a sequence of the method in accordance with the first embodiment of the present invention.

First, an apparatus to be inspected is selected by controlling the six-way valve 66 to which the atmosphere extraction lines 64A to 64E are connected in common (step S1). Thus, an atmosphere to be inspected is selected out of the processing apparatuses 12A to 12D and the clean room 4.

Next, the atmosphere of the selected apparatus is introduced by the gas exhaust pump 52 in the gas exhaust system 36 to be made to pass through the adsorptive material 22 inside the collector 20. At this time, all organic gas materials in the atmosphere to be inspected are adsorbed, whereby a collected organic gas is obtained. The atmosphere having passed through the collector 20 is discharged outside through the gas exhaust line 44 (step S2). The collecting operation is performed for a predetermined time (e.g., a time required to discharge the atmosphere of approximately ten liters, which is about thirty minutes) (step S3). Then, the operation of the gas exhaust pump 52 is stopped to thereby terminate the introduction of the atmosphere to be inspected (step S4).

Thereafter, the heater 24 heats the adsorptive material 22 in the collector 20 to a first temperature to desorb the organic gas materials with relatively low boiling points (step S5). The first temperature is a constant temperature within a range from 60° C. to 200° C. as described above with reference to FIG. 6. Alternatively, the temperature may be changed within this temperature range during the heating. Meanwhile, the carrier gas, e.g., $N_2$ gases, is supplied from the carrier gas supplying unit 32 to the collector 20. Then, the carrier gas is mixed with the desorbed gas, and is discharged through the gas line in the gas mixing system 38 (step S6). When discharging the carrier gas, the switching valve 30 in the gas inlet line 26 is closed to prevent a back flow of the carrier gas into the apparatus. At this time, the concentration measuring unit 56 does not operate, and therefore, the organic gas is discharged without performing the concentration measurement.

Alternatively, the mixed gas may be discharged directly from the gas exhaust system 36 to the outside without going through the gas mixing system 38. The heating of the adsorptive material 22 to the first temperature is performed for a predetermined time, e.g., about ten minutes (step S7). By the heating of the first temperature, most of the organic gas materials with relatively low boiling points are desorbed and discharged in a gaseous form, as shown in the temperature profile of FIG. 6.

Subsequently, by raising the heating temperature to a second temperature, all of the organic gas materials remaining in the adsorptive material 22 are desorbed, thereby forming the desorbed gas (step S8). The carrier gas is continuously supplied during this step as well. Meanwhile, the carrier gas, for example, $N_2$ gas, is supplied from the carrier gas supplying unit 32 to the collector 20. Then, the carrier gas is mixed with the desorbed gas, and then discharged through the gas line 46 in the gas mixing system 38. Further, while the temperature is raised to the second temperature, the concentration measuring unit 56 is operated to start measuring the organic gas concentration (step S9), and this measuring operation continues for a predetermined time, e.g., about ten minutes (step S10).

The second temperature is a temperature at which all of the organic gas materials, including those with relatively high boiling points, can be desorbed; and is, e.g., 200° C. or above as shown in FIG. 6. Here, the higher the second temperature becomes, the higher the desorption efficiency of the organic gas becomes. However, the upper limit of the second temperature is preferably 400° C. in that the desorption efficiency is saturated at 400° C. When the concentration measurement of the organic gas is completed, the supply of the carrier gases is stopped to thereby terminate the measurement process (step S11).

Next, the control unit 58 estimates the lifetime of the organic gas removal filter, which is the present object of the measurement, on the basis of the measurement result obtained by the concentration measuring unit 56 (step S12). This is performed by comparing the measurement result to the reference value of the lifetime inputted from outside in advance. It is preferable that the reference value of the lifetime is set to be, e.g., the gas concentration at the timing when the removal rate indicated by the characteristic curve M (shown in FIG. 3) of the organic gas materials with high boiling points drops down to 80%. In this case, if the concentration in the measurement result is lower than the reference value of the lifetime, the lifetime has not yet expired; otherwise, the lifetime has expired.

Thereafter, the estimation result is stored in the memory or the like, and at the same time, is displayed on the display unit 60 to let the operator be informed of it (step S13). Then, if the measurement result indicates the end of the lifetime, the alarm unit 62 is operated to let the operator be informed (step S14). A series of operations described above are executed for the organic gas removal filter in each of the apparatuses (NO in step S15). If the measurements for the organic gas removal filters in all of the apparatuses are completed (YES in step S15), the concentration measurement is terminated. It is preferable that the concentration measurement is performed, e.g., once a day.

As mentioned above, the collected organic gas is obtained by having the atmosphere to be inspected pass through the adsorptive material 22 inside the collector 20. Then, the desorbed gas is obtained from the collected organic gas by heating the adsorptive material 22. Further, the concentration of the organic gas in the carrier gas that is carrying the desorbed gas is measured. Thereby, the organic gas in the atmosphere to be inspected can be measured in real time.

Further, without measuring the concentration of the organic gas desorbed when the adsorptive material 22 is heated to the first temperature, only that of the organic gas desorbed when the adsorptive material 22 is heated to the second temperature is measured. Therefore, the concentration of only such organic gas materials that have specific properties can be measured. Here, the measured organic gas materials have relatively high boiling points, and therefore tend to be easily adsorbed onto the wafer surface. In this manner, it is possible to determine in real time whether the organic gas removal filter has reached its lifetime, i.e. whether it has entered a breakthrough state or not.

Moreover, the measuring operation of the organic gas concentration and the estimating operation of the lifetime of the organic gas removal filter can be easily performed without requiring additional works. Accordingly, the apparatus cost and the running cost can be greatly reduced.

In accordance with the conventional methods of measuring the organic gas concentration without considering the boiling point, the concentration of all organic gas materials collected by the adsorptive material is measured, and the lifetime of the organic gas removal filter is estimated based on the measurement result obtained as such. Therefore, for example, the concentration of the organic gas materials having low boiling points, which are hardly adsorbed onto the wafer surface, is also included in the measurement value. In this case, even when the lifetime of the organic gas removal filter does not actually come to an end, it is wrongly estimated to have expired. Therefore, the replacement of the organic gas removal filter is performed more frequently than necessary, which causes an increase in running cost. However, in accordance with the present embodiment, the problems discussed above can be avoided, and thus the running cost can be suppressed.

Second Embodiment

In the first embodiment, all of the organic gas materials are collected by the adsorptive material 22, but the concentration of only those with relatively high boiling points in the desorbed gases is measured in the gas concentration measurement process. However, in accordance with the second embodiment, the adsorptive material 22 is heated to a predetermined temperature for collecting organic gas, and only such gas materials with specific properties (e.g., organic gas materials with relatively high boiling points) are collected.

In other words, in the second embodiment, the organic gas is collected by first heating the adsorptive material to a third temperature. Then, the desorbed gas is obtained by heating the adsorptive material to the second temperature higher than the third temperature. Thereafter, the concentration of organic gas in the carrier gas, which is carrying the desorbed gas, is measured. Herein, the third temperature is determined such that organic gas materials with relatively low boiling points are not collected by the adsorptive material. The second temperature is set such that organic gas materials with relatively high boiling points are desorbed.

To be more specific, in collecting the organic gas, the adsorptive material 22 is heated to and maintained at the third temperature so that only such organic gas materials with relatively high boiling points, not those with relatively low boiling points, can be collected. For example, the third temperature is within a range from 60° C. to 200° C. As mentioned above, the second temperature is within a range from 200° C. to 400° C.

Figure 8:
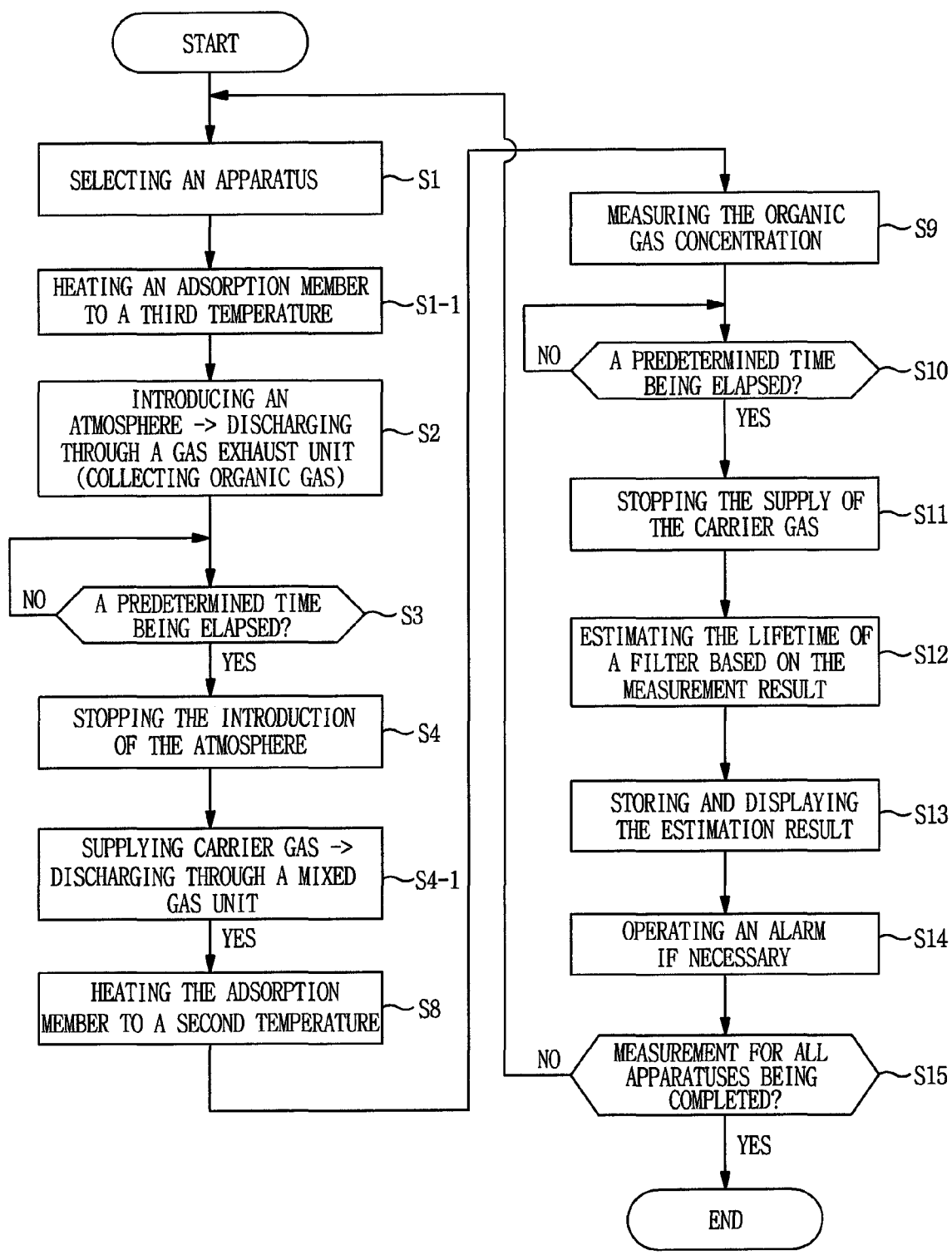
FIG. 8 is a flow chart for illustrating a sequence of the method in accordance with the second embodiment of the present invention.

FIG. 8 is a flow chart for illustrating a sequence of a method in accordance with the second embodiment of the present invention. In FIG. 8, steps identical or similar to those in FIG. 7 are assigned the same step numbers.

First, in the same manner as the first embodiment, an apparatus to be inspected is selected by controlling the six-way valve 66 (step S1). Then, the adsorptive material 22 in the collector 20 is heated to the third temperature by the heater 24 (step S1-1). For example, the third temperature is within a range from 60° C. to 200°, so that the organic gas materials with relatively low boiling points are not trapped, but only those with relatively high boiling points are trapped by the adsorptive material 22.

Next, the atmosphere in the selected apparatus is introduced by the gas exhaust pump 52 in the gas exhaust system 36, and is made to pass through the adsorptive material 22 inside the collector 20. At this time, all of the organic gas materials with relatively high boiling points in the atmosphere are adsorbed, thereby obtaining a collected organic gas. The atmosphere having passed through the collector 20 is discharged outside through the gas exhaust line 44 (step S2). The collecting operation is performed for a predetermined time (e.g., a time required to discharge the atmosphere of approximately ten liters, which is about thirty minutes) (step S3). Then, the operation of the gas exhaust pump 52 is stopped to terminate the introduction of the atmosphere to be inspected (step S4).

Thereafter, the carrier gas is supplied from the carrier gas supplying unit 32, is made to pass through the collector 20, and then is discharged through the gas mixing system 38 (step S4-1). When discharging the carrier gas, the switching valve 30 in the gas inlet line 26 is closed to prevent a back flow of the carrier gas into the apparatus. Simultaneously with the supply of the carrier gas, the adsorptive material 22 is heated to the second temperature, e.g., 200° C. to 400° C., whereby the organic gas materials with relatively high boiling points collected by the adsorptive material 22 are desorbed to form a desorbed gas (step S8).

Then, the processes for measuring the concentration of the organic gas and estimating the lifetime of the organic gas removal filter (steps S9 to S15) are performed, which are identical to those (steps S9 to S15) in the first embodiment shown in FIG. 7. In accordance with the second embodiment, the same effects as those in the first embodiment can be achieved.

Third Embodiment

In the aforementioned first and second embodiments, the adsorptive material 22 is heated in two steps, and the concentration of the organic gas materials with relatively high boiling points is measured. On the contrary, in the third embodiment, the concentration of the organic gas materials with relatively low boiling points is measured.

More specifically, in accordance with the third embodiment, an atmosphere to be inspected is introduced by the gas exhaust pump 52 in the gas exhaust system 36, and all organic gas materials in the atmosphere are adsorbed by the adsorptive material 22 to thereby form a collected organic gas. Subsequently, by heating the adsorptive material 22 using the heater 24 to the first temperature, e.g., 60° C. to 200° C., organic gas materials with relatively low boiling points are desorbed from the adsorptive material 22 to form a desorbed gas. Further, the carrier gas, together with the desorbed gas, is transferred to the concentration measuring unit 56, and then the concentration of organic gas is measured. In this manner, the concentration of the organic gas materials with relatively low boiling points can be measured. This method can be used, for example, to control the concentration of an organic solvent such as a developing solution, or to detect a leak of the organic solvent.

Fourth Embodiment

There are cases where the lifetime of the organic gas removal filters 6 and 14A to 14D need not be estimated. In order to, for example, measure the concentration of organic materials in the atmosphere of the clean room 4, the following method may be used. First, for example, all organic gas materials in the atmosphere of the clean room 4 are trapped by the adsorptive material 22. Thereafter, the adsorptive material 22 is heated by the heater 24 to the second temperature, e.g., 200° C. or higher, to thereby desorb all the organic gas materials, and the concentration thereof is then measured by the concentration measuring unit 56.

Figure 9:
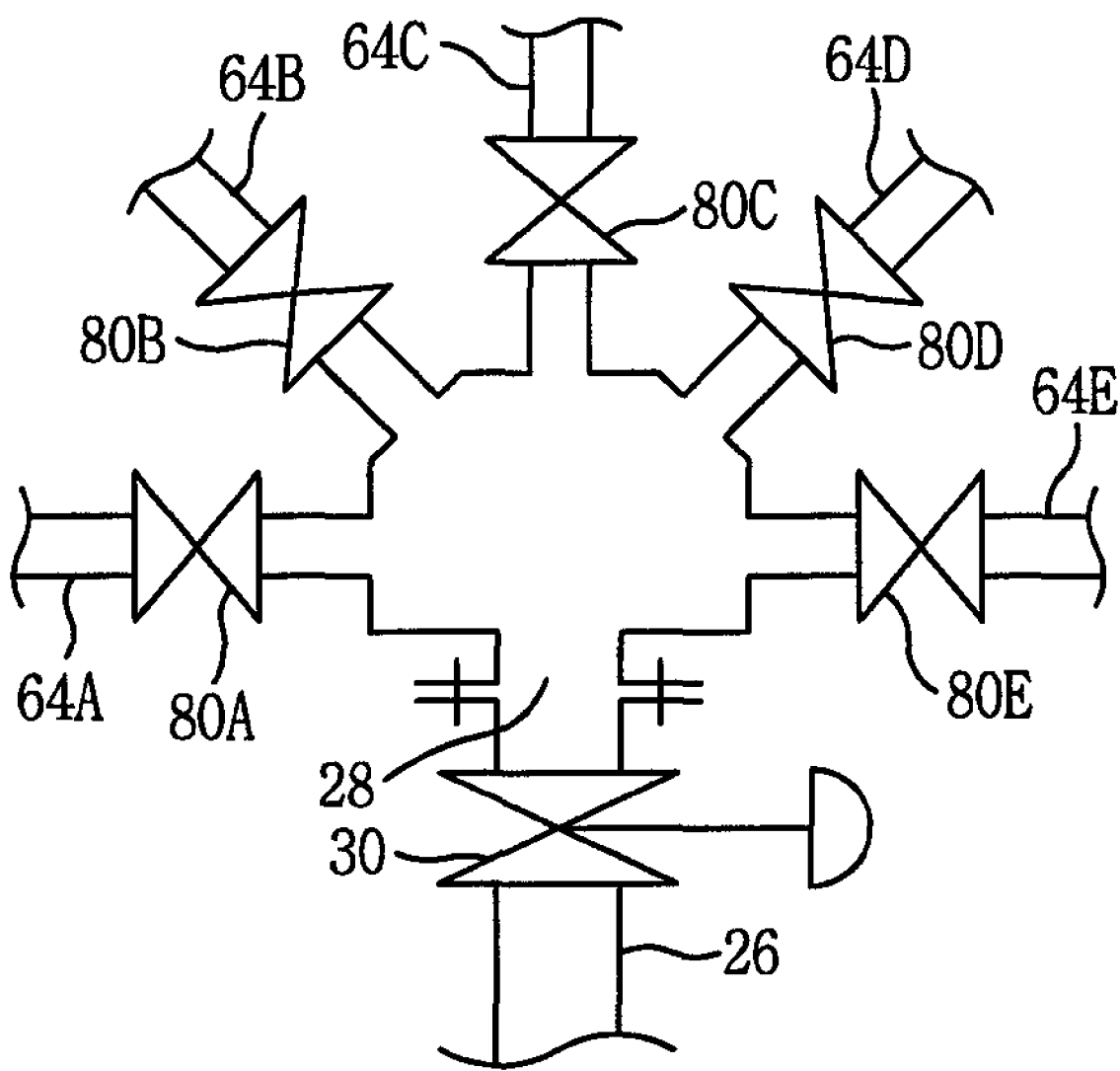
FIG. 9 shows a modified example of a selection mechanism disposed between a concentration measuring apparatus and space to be inspecteds.

Further, in the above described embodiments, the six-way valve 66 serving as the selection valve is disposed in order to select one of the atmosphere extraction lines 64A to 64E. However, it is also possible that a modified example of the selection mechanism shown in FIG. 9 is used instead thereof. In this modified example, switching valves 80A to 80E are disposed at the atmosphere extraction lines 64A to 64E, respectively. One of the atmosphere extraction lines can be selected by selectively opening and closing the switching valves 80A to 80E.

Furthermore, in accordance with the above embodiments, one of the five atmospheres is selected to estimate the lifetime of its organic gas removal filter. However, in case of measuring only a single atmosphere to be inspected, it is preferable to connect the gas inlet port 28 in the gas inlet line 26 coupled to the collector 20 directly to the part to be inspected. Further, the switching valve 50 in the gas exhaust system 36 and the switching valve 54 in the gas mixing system 38 can be integrally formed by, for example, a single number of three-way valve.

(Concentration Measurement of Amine Gas)

Generally, a developing solution for use in a manufacturing process of a semiconductor apparatus such as an IC includes organic amine. Since the amine component deteriorates especially the resolution of chemically amplified resists, it needs to be removed from a clean room or a processing apparatus. Organic amine includes, e.g., trimethylamine and dimethylamine.

Figure 10:
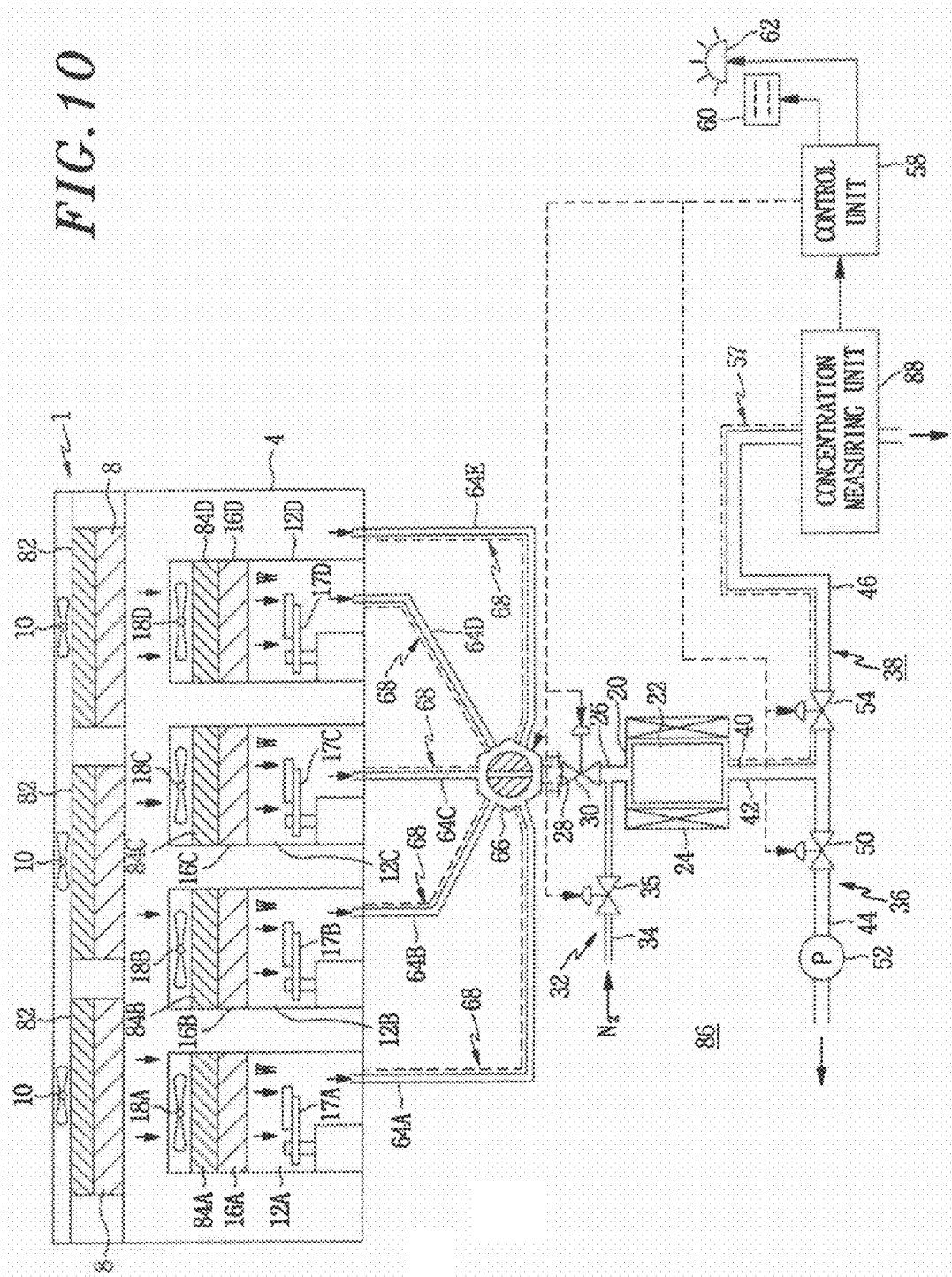
FIG. 10 is a configuration view showing the relationship among an amine gas concentration measuring apparatus, a processing apparatus and a clean room in a processing system in accordance with another embodiment of the present invention.

FIG. 10 is a configuration view showing the relationship among an amine gas concentration measuring apparatus, a processing apparatus and a clean room in a processing system in accordance with another embodiment of the present invention. A processing system 1 and a concentration measuring apparatus 2 shown in FIG. 10 are configured to be basically the same as those of FIG. 1 except some parts for dealing with amine gas. That is, in order to remove amine gas, amine gas removal filters 82 and 84A to 84D are installed in place of the organic gas removal filters 6 and 14A to 14D of FIG. 1, respectively. Further, the amine gas removal filters 82 and 84A to 84D use chemical filters based on activated carbon specially processed for collecting amine.

An amine gas concentration measuring apparatus 86 includes a concentration measuring unit 88 for detecting the CN group in amine, instead of the concentration measuring unit 56 shown in FIG. 1. Further, the parts for collecting amine gas have the same configuration as that of FIG. 1. Specifically, a collector 20 accommodates an adsorptive material 22, and a heater 24 for heating and desorbing a collected amine gas is installed around an outer periphery of the collector 20. Here, a nitrogen phosphorous detector as well known may be used as the concentration measuring unit 88. The chromatography analysis is difficult to perform because amine gas is easily decomposed. However, in the method of the present embodiment, the decomposed amine is indicated by one peak in measuring the total amount of amine.

Figure 11A:
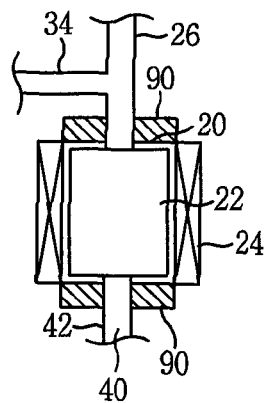
FIG. 11A shows a modified example of a collector in the concentration measuring apparatus.
Figure 11B:
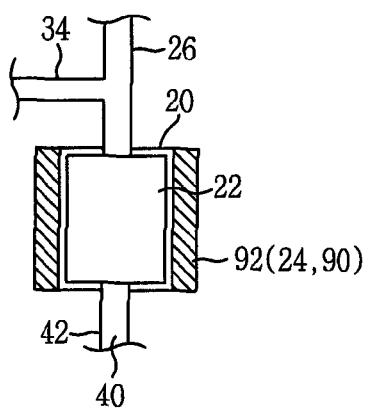
FIG. 11B shows another modified example of the collector in the concentration measuring apparatus.

Further, since it is comparatively more difficult to collect amine gas than other kinds of organic gas, it may be preferable to facilitate the collection of amine gas by, during collecting amine gas, cooling the collector 20 and the adsorptive material 22 therein. FIGS. 11A and 11B illustrate two modified examples of the collector in the concentration measuring apparatus in accordance with the present embodiment.

In the modified example shown in FIG. 11A, a cooler 90 is installed outside of the collector 20 as a distinct body separated from the heater 24. By installing the cooler 90, the collector 20 and the adsorptive material 22 are cooled when collecting amine gas, thereby making it possible to collect the amine gas efficiently. Especially, such amine gas materials with relatively low boiling points can be collected more efficiently.

The cooling temperature of the cooler 90 is dependant on the coolant, and the cooler 90 can be cooled down to about −160° C. when using liquid nitrogen. When collecting amine gas, the temperature of the cooler 90 and the heater 24 is set within a range from −130° C. to 60° C., and preferably, from −30° C. to 40° C. Further, when desorbing amine gas, the heating temperature of the heater 24 is set within a range from 60° C. to 300° C.

In the modified example shown in FIG. 11B, a thermoelectric conversion element 92 is installed outside of the collector 20, wherein the thermoelectric conversion element 92 is formed as a single unit having the functions of both the heater 24 and the cooler 90. A Peltier element may be used as the thermoelectric conversion element 92. The thermoelectric conversion element 92 can function as the heater 24 and the cooler 90 by changing the direction of current. If the thermoelectric conversion element 92 uses the Peltier element, it can be cooled down to −35° C. to −50° C. in case of cooling, and heated up to 70° C. to 150° C. in case of heating.

Figure 12:
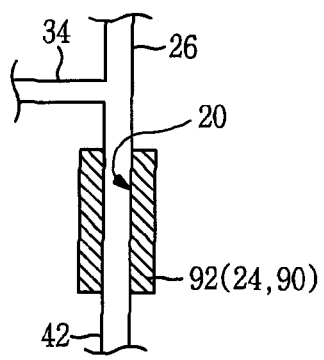
FIG. 12 shows still another modified example of the collector in the concentration measuring apparatus.

In the above-described embodiments, the collector 20 has a large inner volume to accommodate therein the adsorptive material 22, but its structure is not limited thereto. FIG. 12 shows still another modified example of the collector in the concentration measuring apparatus. In the modified example shown therein, a part of the gas inlet line 26 or the discharge line 42 serves as the collector 20. Further, the thermoelectric conversion element 92 described in FIG. 11B, which functions as both the heater 24 and the cooler 90, is installed around the outer periphery of the collector 20.

In this case, amine gas is adsorbed onto and collected by the pipe wall of the line that forms the collector 20. With this configuration, the adsorptive material 22 can be omitted, and the line itself can be used as the collector 20. Therefore, the configuration of the apparatus can be made simple. The adsorption member for adsorbing organic gas may be of various types with the function of either a chemical or physical adsorption or both.

Although the above embodiments have been described with respect to the semiconductor wafer as a target object, an LCD substrate, a glass substrate, a ceramic substrate or the like may also be used as the target object.

INDUSTRIAL APPLICABILITY

The present invention is applied to an apparatus and method for measuring the organic gas concentration of an atmosphere to be inspected taken out from a space to be inspected in a processing system such as a semiconductor processing system or the like.

What is claimed is:

1. A concentration measuring apparatus for measuring a concentration of organic gas contained in an atmosphere to be inspected taken out from a space to be inspected in a processing system, the apparatus comprising:
   a collector having an inlet port connected to the space to be inspected for introducing thereto the atmosphere to be inspected;
   a gas exhaust system, connected to the collector, for exhausting an inside of the collector;
   an adsorption member, accommodated in the collector, for adsorbing organic gas included in the atmosphere to be inspected to obtain a collected gas;
   a temperature control unit having a heater for controlling an adsorption and a desorption of organic gas by adjusting the temperature of the adsorption member;
   a carrier gas supplying unit for supplying the collector with a carrier gas for conveying a desorbed gas desorbed from the adsorption member by heating the adsorption member;
   a concentration measuring unit, connected to the collector, for measuring the concentration of organic gas in the carrier gas that is carrying the desorbed gas; and
   a control unit for controlling the concentration measuring apparatus,
   wherein the control unit controls the concentration measuring apparatus such that, after the collected organic gas is obtained, a first desorbed gas is taken out by heating the adsorption member to a first temperature and is conveyed by the carrier gas; and thereafter a second desorbed gas is taken out by heating the adsorption member to a second temperature higher than the first temperature, and meanwhile the concentration measuring unit measures the concentration of organic gas in the carrier gas that is carrying the second desorbed gas,
   wherein the first temperature is set within a range from 60° C. to 200° C. to desorb an organic gas material having a relatively low boiling point, and the second temperature is set within a range from 200° C. to 400° C. to desorb an organic gas material having a relatively high boiling point, and
   wherein the atmosphere to be inspected is an atmosphere that has passed through an organic gas removal filter, and the control unit has a function of a lifetime estimation for estimating a lifetime of the organic gas removal filter based on a measurement result of the concentration measurement unit.

2. The concentration measuring apparatus of claim 1, further comprising a heating unit for preventing a liquefaction of organic gas, disposed at either or both of a line that connects the collector to the concentration measuring unit and a line that connects the collector to the space to be inspected.

3. The concentration measuring apparatus of claim 1, wherein the inlet port is selectively connected to one of a clean room in a semiconductor processing system and atmospheric transfer chambers in a processing apparatus such that one of the clean room and the atmospheric transfer chambers is selected as the space to be inspected.

4. The concentration measuring apparatus of claim 1, wherein the adsorption member has either a chemical or physical adsorption function or both.

5. A concentration measuring apparatus for measuring a concentration of organic gas contained in an atmosphere to be inspected taken out from a space to be inspected in a processing system, the apparatus comprising:
   a collector having an inlet port connected to the space to be inspected for introducing thereto the atmosphere to be inspected;
   a gas exhaust system, connected to the collector, for exhausting an inside of the collector;
   an adsorption member, accommodated in the collector, for adsorbing organic gas included in the atmosphere to be inspected to obtain a collected gas;
   a temperature control unit having a heater for controlling an adsorption and a desorption of organic gas by adjusting the temperature of the adsorption member;
   a carrier gas supplying unit for supplying the collector with a carrier gas for conveying a desorbed gas desorbed from the adsorption member by heating the adsorption member;
   a concentration measuring unit, connected to the collector, for measuring the concentration of organic gas in the carrier gas that is carrying the desorbed gas; and
   a control unit for controlling the concentration measuring apparatus,
   wherein the control unit controls the concentration measuring apparatus such that the collected gas is obtained by heating the adsorption member to a first temperature, and thereafter the desorbed gas is taken out by heating the adsorption member to a second temperature higher than the first temperature, and meanwhile the concentration measuring unit measures the concentration of organic gas in the carrier gas that is carrying the desorbed gas,
   wherein the first temperature is set within a range from 60° C. to 200° C. so that an organic gas material having a relatively low boiling point is not collected by the adsorption member, and the second temperature is set within a range from 200° C. to 400° C. to desorb an organic gas material having a relatively high boiling point, and
   wherein the atmosphere to be inspected is an atmosphere that has passed through an organic gas removal filter, and the control unit has a function of a lifetime estimation for estimating a lifetime of the organic gas removal filter based on a measurement result of the concentration measurement unit.

6. The concentration measuring apparatus of claim 5, further comprising a heating unit for preventing a liquefaction of organic gas, disposed at either or both of a line that connects the collector to the concentration measuring unit and a line that connects the collector to the space to be inspected.

7. The concentration measuring apparatus of claim 5, wherein the inlet port is selectively connected to one of a clean room in a semiconductor processing system and atmospheric transfer chambers in a processing apparatus such that one of the clean room and the atmospheric transfer chambers is selected as the space to be inspected.

8. The concentration measuring apparatus of claim 5, wherein the adsorption member has either a chemical or physical adsorption function or both.

* * * * *